US010264793B2

(12) United States Patent
Meccia et al.

(10) Patent No.: US 10,264,793 B2
(45) Date of Patent: Apr. 23, 2019

(54) ANTIMICROBIAL COPPER COMPOSITIONS AND THEIR USE IN TREATMENT OF FOODSTUFFS AND SURFACES

(71) Applicant: CMS TECHNOLOGY, INC., New York, NY (US)

(72) Inventors: John Meccia, Ringoes, NJ (US); Ronald C. Shapira, New York, NY (US); Francis Dautreuil, Seabrook, TX (US); James Dietrich, Harrisburg, PA (US)

(73) Assignee: CMS TECHNOLOGY, INC., New York, NY (US)

( * ) Notice: Subject to any disclaimer, the term of this patent is extended or adjusted under 35 U.S.C. 154(b) by 0 days.

(21) Appl. No.: 15/529,265

(22) PCT Filed: Nov. 25, 2015

(86) PCT No.: PCT/US2015/062586
§ 371 (c)(1),
(2) Date: May 24, 2017

(87) PCT Pub. No.: WO2016/086087
PCT Pub. Date: Jun. 2, 2016

(65) Prior Publication Data
US 2017/0258093 A1     Sep. 14, 2017

Related U.S. Application Data

(60) Provisional application No. 62/084,278, filed on Nov. 25, 2014.

(51) Int. Cl.
| | |
|---|---|
| *A01N 59/20* | (2006.01) |
| *A23L 3/358* | (2006.01) |
| *A23L 3/3508* | (2006.01) |
| *A23B 4/20* | (2006.01) |
| *A23B 5/14* | (2006.01) |
| *A23B 7/154* | (2006.01) |
| *A23B 9/26* | (2006.01) |

(52) U.S. Cl.
CPC ............... *A01N 59/20* (2013.01); *A23B 4/20* (2013.01); *A23B 5/14* (2013.01); *A23B 7/154* (2013.01); *A23B 9/26* (2013.01); *A23L 3/358* (2013.01); *A23L 3/3508* (2013.01); *A23V 2002/00* (2013.01); *Y02A 40/943* (2018.01)

(58) Field of Classification Search
CPC .. A01N 59/20; A23B 9/26; A23B 4/20; A23B 5/14; A23L 3/358; A23V 2002/00
USPC ......................................................... 424/637
See application file for complete search history.

(56) References Cited

U.S. PATENT DOCUMENTS

| 5,997,911 A | 12/1999 | Brinton | |
|---|---|---|---|
| 6,432,892 B2 * | 8/2002 | Meine | C11D 1/662 426/478 |
| 2006/0189483 A1 | 8/2006 | Hickok | |
| 2007/0269563 A1 * | 11/2007 | Mixon | A23B 4/20 426/332 |
| 2008/0292673 A1 | 11/2008 | Crudden | |
| 2011/0206790 A1 | 8/2011 | Weiss | |
| 2012/0060258 A1 | 3/2012 | Stewart | |
| 2014/0322352 A1 | 10/2014 | Creasey | |

FOREIGN PATENT DOCUMENTS

| JP | 6-153744 | 6/1994 |
|---|---|---|
| WO | WO-02/096202 | 12/2002 |

OTHER PUBLICATIONS

Authors: Rabin Gyawali and Salam A. Ibrahim; title: Synergistic effect of copper and lactic acid against *Salmonella* and *Escherichia coli* O157:H7: A review; Emir. J. Food Agric. Nutrition and Food Science, vol. 24 (1), pp. 01-11, 2012. (Year: 2012).*
Ritsuko et al., "Inactivation of Cryptosporidium parvum Oocysts by Copper Ions", Journal of the Japanese Association of Infectious Diseases, vol. 78, No. 2, Feb. 2004.
Millero, F. J. "Sea water as an electrolyte". Chemistry of Marine Water and Sediments. Springer-Verlag, Berlin, Heidelberg. 2002. 3-34.
Jack Bone et al., "Synthesis and Biotesting of Metallic Surfactants" Journal of the American Pharmaceutical Association, Scientific Edition, vol. XLVII, No. 11, XP55538411, Nov. 1, 1958, pp. 795-799.

* cited by examiner

*Primary Examiner* — Yanzhi Zhang
(74) *Attorney, Agent, or Firm* — BakerHostetler

(57) ABSTRACT

The present disclosure provides compositions for antimicrobial use comprising a mineral acid, an organic acid, or a combination thereof; a copper(II) salt; and a buffering salt, a detergent, or a combination thereof. The present disclosure also provides methods for reducing the number of pathogens on a surface by applying compositions of the present disclosure to the surface.

18 Claims, 3 Drawing Sheets

ANTIMICROBIAL COPPER COMPOSITIONS AND THEIR USE IN TREATMENT OF FOODSTUFFS AND SURFACES

CROSS-REFERENCE TO RELATED APPLICATIONS

This application is the National Stage Application of International Patent Application No. PCT/US2015/062586, filed Nov. 25, 2015, which claims the benefit of U.S. Provisional Application No. 62/084,278, filed on Nov. 25, 2014, the entirety of which is incorporated by reference herein.

FIELD

The disclosure is in the field of antimicrobial treatments of foodstuffs and hard surfaces using compositions comprising a mineral acid, an organic acid, or a combination thereof; a copper(II) salt; and a buffering salt, a detergent, or a combination thereof.

BACKGROUND

Contamination of surfaces by toxic levels of bacteria, viruses, and parasites ("pathogens") is a significant concern. Antimicrobial compositions used in the food industry must not only be capable of reducing the number of surface pathogens, they must be safe for human consumption. In addition, antimicrobial compositions should not detrimentally affect the quality of the foodstuff or surface being treated. Antimicrobial compositions for use on foodstuffs and surfaces should also be easy to apply and be relatively inexpensive to ensure they are economical for the intended output.

Thus, there is a need for antimicrobial compositions that are safe, effective, easy to apply, and economical/commercially viable. The disclosure is directed to these and other important needs.

SUMMARY

The present disclosure provides compositions comprising a mineral acid, an organic acid, or a combination thereof; a copper(II) salt; and a buffering salt, a detergent, or a combination thereof. Methods of using these compositions to reduce the number of pathogens on surfaces are also described.

The general description and the following detailed description are exemplary and explanatory only and are not restrictive of the invention, as defined in the appended claims. Other aspects of the present invention will be apparent to those skilled in the art in view of the detailed description of the invention as provided herein.

DETAILED DESCRIPTION OF ILLUSTRATIVE EMBODIMENTS

Figure 1:
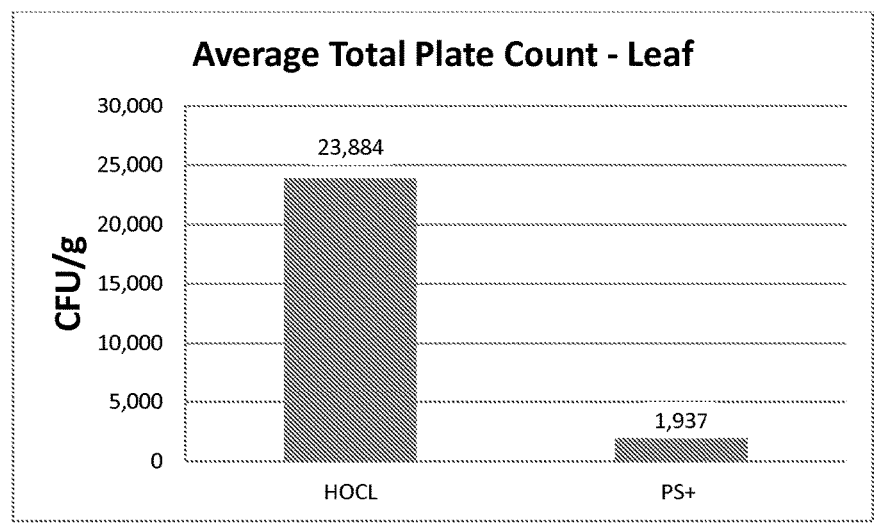
FIG. 1 depicts the results of individual trials (214 data points) at a pH of 2.2 of wash water samples formulated with a composition of the disclosure.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As used herein, "foodstuffs" refers to solid and liquid food products that are edible by humans or domesticated animals. Solid food products include but are not limited to meat products such as poultry products (e.g., chicken, duck, and turkey products), eggs, beef products, pork products, and seafood products (e.g., fish, shellfish, crustaceans, mollusks, echinoderms, seaweed). Solid food products also include produce products, for example, fruits, vegetables, algae, seeds, grains, sprouts, legumes, soy, and nuts. Solid food products also include dairy products such as hard, soft, and semi-soft cheeses. Liquid food products can include beverages (e.g., juices, soda), liquid dairy products (e.g., milk and cream), fermented beverages (e.g., beer and wine), and liquid feed ingredients and liquid feeds used as animal feed (e.g. fermented liquid feeds fed to farm livestock and poultry).

As used herein, "hard surfaces" refers to surfaces including but not limited to wood (hardwood and engineered), travertine, MDF (medium density fiberboard), plywood, ceramic, concrete, porcelain, linoleum, laminates, granite, marble, quartz, soapstone, stainless steel, copper, metal alloys, iron, plastic, brick, other masonry, sheetrock, plaster, glass, card stock, corrugated fiberboard, paperboard, rubber, latex, plastic, composite materials that may include two or more of the above materials, and the like.

As used herein, "pathogens" include bacteria, viruses, and parasites. Examples of bacteria that can be reduced using the compositions of the disclosure include gram positive bacteria and gram negative bacteria, for example, *Salmonella enterica*, *Listeria monocytogenes*, *Escherichia coli*,

*Clostridium botulinum, Clostridium difficile, Campylobacter, Bacillus cereus, Vibrio parahaemolyticus, Vibrio cholerae, Vibrio vulnificus, Staphylococcus aureus, Yersinia enterocolitica, shigella*, and combinations thereof. Examples of *Salmonella enterica serovars* that can be reduced using the compositions of the disclosure include, for example, *Salmonella Enteriditis, Salmonella Typhimurium, Salmonella Poona, Salmonella Heidelberg*, and *Salmonella Anatum*. Examples of viruses that can be reduced using the compositions of the disclosure include enterovirus, norovirus, influenza, rotavirus, or combinations thereof. Examples of parasites include *Cryptosporidium, Toxoplasma gondii, Giardia duodenalis, Cyclospora cayetanensis, Trichinella spiralis, Taenia saginata, Taenia solium*, or combinations thereof.

In one aspect, the present disclosure provides compositions comprising a mineral acid, an organic acid, or a combination thereof; a copper(II) salt; and a buffering salt, a detergent, or a combination thereof. In preferred embodiments, these compositions exclude chlorine and sources of chlorine. For example, preferred compositions of the invention exclude hypochlorite salts such as sodium hypochlorite and calcium hypochlorite.

Preferred mineral acids are known in the art. Mineral acids useful in the disclosed compositions and methods will have a pKa of less than or equal to 1. Preferred mineral acids include, for example, sulfuric acid, phosphoric acid, hydrochloric acid, nitric acid, boric acid, hydrobromic acid, perchloric acid, hydroiodic acid, and combinations thereof. In some aspects, the mineral acid is sulfuric acid. In other aspects, the mineral acid is phosphoric acid. In yet other aspects, the mineral acid is hydrochloric acid. The mineral acid can be present in any amount so as to achieve a predetermined pH, as described herein. In some embodiments, the mineral acid is present in a concentration of between about 0.1 and about 3 wt. %, preferably about 0.1 and about 1 wt. %, based on the weight of the composition.

Preferred organic acids are known in the art. Organic acids useful in the disclosed compositions and methods will have a pKa of between 1 and 7. Organic acids include citric acid, ascorbic acid, lactic acid, acetic acid, peracetic acid, formic acid, propionic acid, butyric acid, valeric acid, caproic acid, oxalic acid, malic acid, benzoic acid, carbonic acid, phenol, uric acid, taurine, p-toluenesulfonic acid, triflic acid, aminomethylphosphonic acid, and combinations thereof. In some aspects, the organic acid is citric acid. In other aspects, the organic acid is ascorbic acid. In still other aspects, the organic acid is lactic acid. In some aspects, the organic acid is acetic acid. In some aspects, the organic acid is peracetic acid. The organic acid can be present in any amount so as to achieve a predetermined pH, as described herein. In some embodiments, the organic acid is present in a concentration of between about 0.1 and about 3 wt. % or between about 0.1 and about 2 wt. %, preferably between about 0.1 and about 1 wt. %, based on the weight of the composition.

The compositions of the disclosure can include a mineral acid or combination of mineral acids. The compositions of the disclosure can include an organic acid or a combination of organic acids. The compositions of the disclosure can include a mixture of mineral acid(s) and organic acid(s). In those embodiments comprising a mixture of mineral acids, a mixture of organic acids, or a mixture of mineral acid(s) and organic acid(s), the total amount of acid is sufficient to achieve a predetermined pH, as described herein. In some embodiments, the combination of acids is at a concentration of between about 0.1 and about 3 wt. %, between about 0.1 and about 2 wt. %, preferably about 0.1 and about 1 wt. %, based on the weight of the composition.

Preferred copper (II) salts include copper (II) sulfate, copper (II) chloride, copper (II) bromide, and the like. A preferred copper (II) salt is copper (II) sulfate, with copper (II)sulfate pentahydrate being particularly preferred. In some aspects, the copper (II) salt is copper (II) chloride. In other aspects, the copper (II) salt is copper (II) bromide. Combinations of copper (II) salts are also within the scope of the disclosure.

The copper salt concentration used in the compositions of the disclosure can be determined by one skilled in the art and will be in an amount effective to achieve pathogen reduction on the particular surface being treated. For example, the copper salt concentration can be up to 1000 ppm, between 500 and 1000 ppm, between 100 and 500 ppm, or between 1 and 100 ppm. According to the disclosure, the copper salt concentration used in the compositions of the disclosure is between about 1 ppm and about 80 ppm, about 1 ppm and about 70 ppm, about 1 ppm and about 60 ppm, about 1 ppm and about 50 ppm, about 1 ppm and about 40 ppm, about 1 ppm and about 30 ppm, about 1 ppm and about 20 ppm, about 1 ppm and about 15 ppm, about 1 ppm and about 10 ppm, about 3 ppm and about 10 ppm, or about 35 ppm and about 40 ppm. Other preferred compositions of the disclosure include about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 ppm of the copper (II) salt. In some embodiments, the copper(II) salt concentration is between about 1 and 19 ppm for fruit and vegetable applications, or between about 1 and less than 60 ppm for meat, seafood, and/or poultry applications.

Preferred buffering salts for use in the disclosure include ammonium sulfate, sodium sulfate, sodium chloride, calcium sulfate, and combinations thereof. Sodium sulfate, ammonium sulfate, and calcium sulfate are particularly preferred buffering salts. In some aspects, the buffering salt is ammonium sulfate. In other aspects, the buffering salt is sodium sulfate. In some aspects, the buffering salt is sodium chloride. In other aspects, the buffering salt is calcium sulfate.

Preferred detergents include compositions at concentrations that are preferably Generally Recognized as Safe by the U.S. Food and Drug Administration. Within the scope of the disclosure, a "detergent" refers to a surfactant or a mixture of surfactants. Particularly preferred detergents for use in the compositions of the disclosure include dodecyl sulfate, n-alkylbenzene dodecyl sulfates, alkyl polyglycosides, sodium lauryl sulfate, polysorbates (for example, polysorbate 20, polysorbate 40, polysorbate 60, and polysorbate 80), and combinations thereof. Particular preferred alkyl polyglycosides include alkyl polyglucoside, decyl polyglucose, lauryl polyglucose, and combinations thereof.

Compositions of the disclosure can include a mineral acid, an organic acid, or a combination thereof; a copper(II) salt, and a buffering salt, while excluding a detergent. Other compositions of the disclosure can include a mineral acid, an organic acid, or a combination thereof; a copper(II) salt; and a detergent, while excluding a buffering salt. Still other compositions of the disclosure can include a mineral acid, an organic acid, or a combination thereof; a copper(II) salt; a buffering salt; and a detergent.

According to the disclosure, the buffering salt and/or detergent are present in the compositions each at concentrations of between 0.01 wt. % and 0.5 wt. %, 0.01 wt. % and 0.4 wt. %, 0.01 wt. % and 0.3 wt. %, 0.01 wt. % and 0.25 wt. %, 0.01 wt. % and 0.20 wt. %, 0.01 wt. % and 0.15 wt. %, or 0.01 wt. % and 0.10 wt. % based on the weight of the composition. Preferred amounts of buffering salts and/or detergents maintain the pH of aqueous compositions of the disclosure within preselected ranges. Preferred amounts of buffering salts and/or detergents can also control surface tension changes to allow for improved reduction of pathogens on a surface. Other preferred compositions of the disclosure include a buffering salt and/or detergent each at a concentration of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.5, 0.6, 0.7, 0.8, 0.9, or 1 wt. %, based on the weight of the composition. Preferred amounts of buffering salts and/or detergents can provide for reduced organoleptic damage at low pH levels and can provide for reduced causticity, reduced toxicity, and safer handling for human workers, which have not been observed with prior compositions used in the art.

Some compositions of the disclosure consist essentially of the mineral acid, the copper (II) salt, and the buffering salt and/or detergent, as described herein. That is, the disclosure envisions compositions that include the mineral acid, the copper (II) salt, and the buffering salt and/or detergent as described herein, and only those additional materials, for example, water, that do not materially affect the basic and novel characteristics of the inventions disclosed herein. Preferably, these compositions exclude chlorine and sources of chlorine such as hypochlorite salts.

Some compositions of the disclosure consist essentially of the organic acid, the copper (II) salt, and the buffering salt and/or detergent, as described herein. That is, the disclosure envisions compositions that include the organic acid, the copper (II) salt, and the buffering salt and/or detergent as described herein, and only those additional materials, for example, water, that do not materially affect the basic and novel characteristics of the inventions disclosed herein. Preferably, these compositions exclude, or contain in minute amounts, chlorine and sources of chlorine such as hypochlorite salts.

In certain embodiments, the compositions of the disclosure that comprise an organic acid, for example ascorbic acid, will possess antioxidative properties. In other embodiments, the compositions can further comprise a non-organic acid antioxidant. Antioxidants that are Generally Recognized As Safe by the FDA are known in the art and include, for example, plant extracts. The antioxidant can be included in a concentration of between about 0.01 wt. % and about 1.0 wt. %, between about 0.01 wt. % and about 0.2 wt. %, between about 0.01 wt. % and about 0.15 wt. %, between about 0.01 wt. % and about 0.10 wt. %, or between about 0.01 wt. % and about 0.05 wt. %.

In some embodiments, preferred compositions of the invention are non-oxidizing and may exclude, or contain in minute amounts, ozone, peracetic acid, chlorine dioxide, and hypochlorite salts. The non-oxidizing compositions of the disclosure are advantageous for water re-circulation applications and can result in significant water savings.

In particularly preferred embodiments, the compositions of the disclosure are aqueous compositions. The concentration of the mineral and/or organic acid, the copper salt, and the buffering salt and/or detergent in the aqueous solutions can vary, based on the particular application in which the aqueous solution is being used. In some embodiments, the ratio of water to the other composition components is about 1:1. In other embodiments, the ratio of water to the other composition components is between 1:1 and 2:1. In other embodiments, the ratio of water to the other composition components is between about 1:1 and about 20:1 or between about 1:1 and about 500:1. In some embodiments, the ratio of water to the other composition components is about 20:1 to about 500:1. The concentrations useful for final applications in aqueous solutions may be lower than the concentrations in an original solid form, which can be diluted about 500-fold, about 450-fold, about 400-fold, about 350-fold, about 300-fold, about 250-fold, about 200-fold, about 150-fold, about 100-fold, about 90-fold, about 80-fold, about 70-fold, about 60-fold, about 50-fold, about 40-fold, about 30-fold, about 20-fold, about 10-fold, about 5-fold, about 4-fold, about 3-fold, or even about 2-fold. Appropriate dilution amounts can be selected based upon the concentrate strength and the expected pathogenic loading of the incoming treated article.

The aqueous solutions of the disclosure can be neutral pH (about pH 7) or acidic pH (pH less than 7) or slightly alkaline pH (pH up to about 9). In preferred embodiments, the pH is between about 1 and 7. In some embodiments, the pH is between about 2 and 7. In other embodiments, the pH is between about 3 and 7. In still other embodiments, the pH is between about 4 and 7. Preferably, the pH of the aqueous solutions of the disclosure is about 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 4, 4.5, 5, 5.5, 6, 6.5, 7, 7.5, 8, 8.5, or about 9. In still other embodiments, the pH of the aqueous solutions of the disclosure are between 1.6 and 6.5, between 2.1 and 6.5, between 1.6 and 4.5, between 1.6 and 3.5, or between 2.0 and 3.0. According to the disclosure, the pH of the aqueous solutions is tested at about 5° C. or about 22° C., depending on the selected application, using methods known in the art. Those skilled in the art readily appreciate that the pH of the aqueous solutions of the disclosure can be adjusted by adjusting the amount of the acid in the solution.

In some embodiments of the disclosure, the compositions can alternatively be in the form of a solid and can be pellets, granules, powders, pods, other dissolvable/water-soluble films or packaging, or tablets. These compositions comprise 10% or less, by weight, of water/moisture. The compositions can be encased in a water-soluble film. Water-soluble films can be formed from, for example, a polyvinyl alcohol film, an aliphatic polyether film, or a polyethylene glycol film. Such films are known in the art. Suitable films will be completely soluble or dispersible in water at temperatures above about 5° C. The films will have a thickness of about 0.5 mils to about 5 mils, preferably from about 1 to 3 mils. The water-soluble films can be sealed using, for example, heat or ultrasonic sealing methods known in the art.

In other aspects the present disclosure provides methods of reducing the number of pathogens on a surface comprising applying any of the compositions of the disclosure to a surface. The surface can be a foodstuff surface or a hard surface. Preferably, the compositions used in the described methods are aqueous solutions. The surfaces can be treated via any means known in the art. For example, in preferred embodiments, any composition of the disclosure can be applied to the surfaces of the foodstuffs via sprinkling, spraying, rinsing, soaking, immersing, washing, or the like. Dip treatments can be used, and include full submersion, whether through mechanical or manual addition, in single or multiple tank designs. Spray applications can be used, and can consist of single or multiple spray nozzles or drip applicators. In some embodiments, spray application can utilize ultrasonic nozzling or can be combined with mechanical abrasion to improve surface area contact.

The aqueous solutions used in the described methods can be at any commercially viable temperature that will not harm the surface to which the aqueous solution will be applied, for example, between about 32° F. (0° C.) and 212° F. (100° C.) or between about 32° F. (0° C.) and 135° F. (57° C.). The solutions can be cold, for example, about 32° F. or about 38° F. (about 3° C.), or warm, for example, about 135° F. In other embodiments, these solutions can be about 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140° F. In yet other embodiments, the aqueous solutions used in the described methods can be at temperatures between about 140 and about 212° F. Higher temperatures can be preferred for use on hard surfaces.

In preferred embodiments, applying comprises submerging the surface for a time sufficient to ensure adequate coverage and/or penetration of the described compositions to and/or in the surface. The submersion times can be up to, for example, 5 minutes, up to about 4 minutes, up to about 3 minutes, up to about 2 minutes, or up to about 1 minute. Submersion times of less than 1 minute are also envisioned and may be as short as two seconds at certain lower pH levels. Preferred submersion times are between about 2 seconds and about 180 seconds, between about 2 seconds and about 120 seconds, between about 2 seconds and about 90 seconds, between about 2 seconds and about 60 seconds, between about 2 seconds and about 45 seconds, or between about 2 seconds and about 30 seconds.

The compositions of the disclosure are effective in reducing the number of pathogens, i.e., microbes, viruses, or parasites on a surface. That is, treating surfaces with compositions of the disclosure reduces the growth and/or propagation of bacteria, viruses, and/or parasites (for example, by killing or materially mitigating the growth of such bacteria, viruses, and/or parasites) on the surface, as compared to a surface that has not been treated with a composition of the disclosure. For example, the compositions of the disclosure are effective in reducing the number of pathogens by about 10%, as compared to a surface that has not been treated with a composition of the disclosure. In other embodiments, the compositions of the disclosure are about 20%, 30%, 40%, 50%, 60%, 70%, 80%, 90%, 100%, 110%, 120%, 130%, 140%, 150%, 160%, 170%, 180%, 190%, 200%, 300%, 400%, 500%, or greater, more effective in reducing pathogens on a surface, when compared to a surface that has not been treated with a composition of the disclosure. The compositions of the disclosure are effective in reducing the number of pathogens by about 10%, about 20%, about 30%, about 40%, about 50%, about 60%, about 70%, about 80%, or about 90% as compared to a surface that has been treated with standard chlorine and citric acid treatment.

Turbid conditions increase the risk of pathogens producing foodborne illness. The compositions of the disclosure are effective in reducing the number of pathogens, even in turbid conditions, for example at food processing facilities.

The following examples are provided to illustrate compositions, processes, and properties described herein. The examples are merely illustrative and are not intended to limit the disclosure to the materials, conditions, or process parameters set forth therein.

EXAMPLES

Example 1: General Bacteria Assay

The Vivione RAPID-B instrument start-up was performed using manufacturer's instructions (Vivione Biosciences, LLC, Pine Bluff, Ark.). Performance Verification was performed per manufacturer's instructions to verify performance and identify any potential problems. The Rapid-B system was then prepped for running General Bacteria Total Plate Count Assays. Treatment solutions were then prepared based on the protocol being tested. Solutions were inoculated 99:1; meaning 99 mL of treatment solution was combined with 1 mL of bacterial bird rinse, creating a $10^{-2}$ dilution. Serial dilutions ($10^{-3}$ dilution was commonly used) were performed using sterile buffered peptone water to amplify the dilution factor. Samples were prepared by combining 570 μl of sterile buffered peptone water, 330 μl of TPC (Total Plate Count) Reagent, and 100 μl from the dilution tube being tested into a reaction tube. This process dilutes the sample an additional $10^{-1}$ (Therefore, $10^{-4}$ was the general dilution tested). The sample reaction tube was left for 15 minutes, being periodically vortexed. The General Bacteria Protocol on the Vivione machine was opened and operational settings confirmed as instructed in the Vivione Biosciences manual. After 15 minutes, the reaction tube was placed on the sample arm and moved into the run position to begin analysis. Once the sample was running, the arm was returned to the flush position to allow for flushing upon completion.

Example 2: Treatment of Leafy Green Vegetables Delays Decay

Wash water was formulated with antimicrobial compositions of the present disclosure, referred to here as Composition A or Composition PS+, and used in a dip tank for treatment of post-harvest leafy green vegetables. Wash water treated with standard chlorine and citric acid treatment was also tested for comparison. The wash water samples were each used in dip tanks at temperatures of approximately 38° F. and were used to treat leafy green vegetables for thirty (30) seconds in turbulent water with over 250 samples taken for results directly from the surface of the leafy green vegetables.

Composition A comprised a mineral acid with low pKa value (sulfuric acid), combined with copper sulfate pentahydrate at 35-40 ppm (copper ion at 9-10 ppm), buffering salt (ammonium sulfate at 0.5 percent) in water at 38° F. The pH of the wash water solution was 2.2.

Composition PS+ comprised a mineral acid with low pKa value (sulfuric acid), combined with copper sulfate pentahydrate at 35-40 ppm (copper ion at 9-10 ppm), buffering salt (ammonium sulfate at 0.05 percent) and surfactant (alkyl polyglycoside) in water at 38° F. The pH of the wash water solution was 2.2.

Leafy green vegetables were treated with either Composition A or with a standard chlorine and citric acid treatment. Following treatment, the leafy green vegetables were inspected for sensory characteristics and visible decay and measured for microbial loading via total plate count (TPC). Results are summarized in Table 1.

TABLE 1

| Day | Average TPC: Composition A Treatment | Composition A Treated Product Sensory Characteristics | Average TPC: Standard Chlorine Treatment | Standard Chlorine Treated Product Sensory Characteristics |
|---|---|---|---|---|
| 0 | 7,265 | Texture: Crisp<br>Color: Bright, Fresh Appearance<br>Odor: No Off-Odor | 208,217 | Texture: Crisp<br>Color: Bright, Fresh Appearance<br>Odor: No Off-Odor |
| 7 | 60,833 | Texture: Crisp<br>Color: Bright, Fresh Appearance<br>Odor: No Off-Odor | 558,100 | Texture: less crisp, less springiness<br>Color: Some decline in appearance (dull)<br>Odor: Slight "musty" |
| 14 | 652,500 | Texture: Crisp<br>Color: Bright, Fresh Appearance<br>Odor: No Off-Odor<br>Visible Decay: <1%<br>Over-all Acceptability: Acceptable with some increase in visible defects | 1,064,652 | Texture: beginning to decline, less crisp, less springiness<br>Color: Less bright, more of a dull appearance<br>Odor: Increasing off-odor<br>Visible Decay: 4-6%<br>Over-all Acceptability: Not Acceptable due to general decline, increased visible defects, Secondary Decay |
| 18 | 4,200,000 | Texture: Crisp<br>Color: Bright<br>Odor: Slight "musty"<br>Visible Decay: less than 3%<br>Over-all Acceptability: Not Acceptable due to general decline, Increased visible defects. | 4,333,333 | Texture: beginning to decline leaf is flaccid, less springiness.<br>Color: less "bright", more of a dull appearance<br>Odor:: Increased Off-Odor, "musty"<br>Visible Decay: 6-8+% and increased "wetness."<br>Over-all Acceptability: Not Acceptable due to general decline, increased visible defects, Severe Decay. |

For products treated with Composition A, there was a materially lower level of TPC at day 0 (7,268 vs 208,217). At day 7, the TPC was still material lower than standard treatment while providing for improved relative texture, color, and odor. At day 15, the TPC remained significantly below standard treatment with a materially improved difference in texture, color, odor, decay and acceptability for commercial use. After 14 to 16 days there was an increase in visible decay, primarily at the cut end of the leaves where the cuts are ragged and crushed, yet still at lower levels and superior texture, color, odor, and decay. There was an apparent reduction in oxidative discoloration in undamaged leaf Standard chlorine-treated leaves began showing a general decline at 10 to 14 days in association with tissue damage. Pockets of secondary decay rapidly advanced in the standard chlorine-treated product, while decay in product treated with Composition A (even at day 20) remained associated with individual leaves.

Wash water samples formulated with Composition PS+ were treated at a pH of 2.2. Subsequent trials showed a significant reduction in Total Plate Count (TPC). The results of individual trials (214 data points) at a pH of 2.2 are shown in FIG. 1. The results demonstrated a 92% reduction in TPC across all trials versus optimized chlorinated treatments of 20 ppm chlorine at a pH of 6.0. The reductions were generally the highest during the most turbid conditions where foodborne illness risks are highest.

Figure 2:
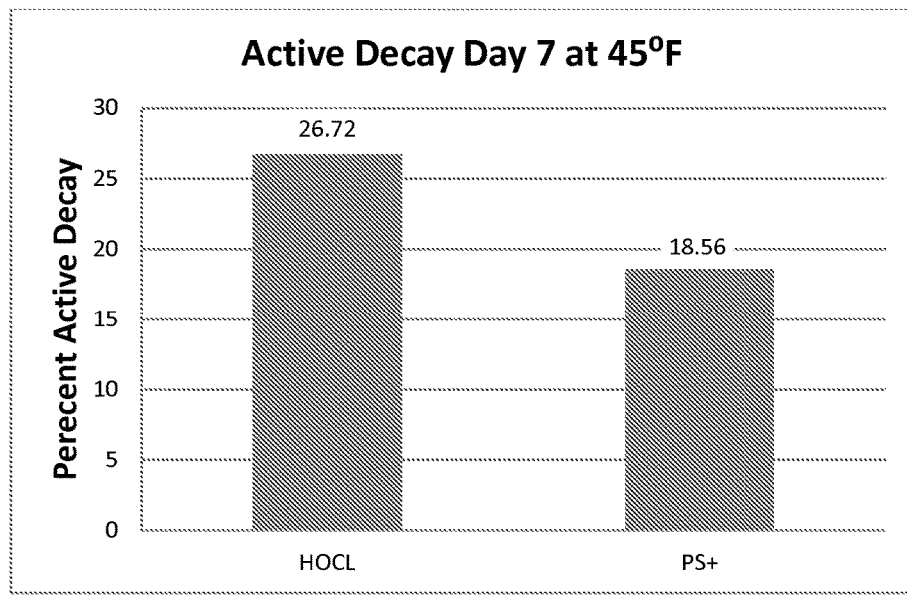
FIG. 2 depicts the results of accelerated shelf-life testing at 45° F. Approximately 30% reduction in active decay was achieved with treatment in antimicrobial solution with a composition of the disclosure compared to a standard hypochlorous acid treatment.

FIG. 2 shows the results of accelerated shelf-life testing at 45° F. Approximately 30% reduction in active decay was achieved with treatment in antimicrobial solution with Composition PS+ compared to the standard hypochlorous acid treatment. While not wishing to be bound by any particular theory, it is speculated that this reductions can be attributed to materially-reduced pathogen load at the onset of treatment.

Example 3: Absence of Organisms in Wash Water Formulated With Antimicrobial Composition of the Disclosure The wash waters with Composition PS+ used in Example 2 were tested for yeast and mold and for Total Plate Count (TPC) following treatments of post-harvest leafy green vegetables. For yeast and mold, colony forming units (CFU)/mL were measured. A limit of detection of 1 CFU/mL was used. Out of thirty (30) samples of wash water treated with Composition PS+, 29 resulted in detection of <1 CFU/mL and 1 resulted in a reported result of 1 CFU/mL, the limit of detection. Standard chlorine-treated wash water indicated <10 CFU/mL for yeast, an average of 55 CFU/mL for mold, and an average of 3,172 for TPC.

Example 4: Significant Reduction of Pathogenic Organisms by Exposure to Antimicrobial Compositions of the Disclosure Challenge cultures were exposed to Composition A and Composition PS+ used in Example 2 at predetermined concentrations and exposure times and then enumerated. The population of the challenge organism prior to exposure was compared to the population present post-exposure to determine the germicidal ability of each composition.

The following challenge microorganisms were evaluated:
Staphylococcus aureus (ATCC #6538)
Listeria monocytogenes (ATCC #7646)
Escherichia coli 0157:H7 (ATCC #35150)
Salmonella enterica serovar Anatum (ATCC #9270)
Methicillin-resistant Staphylococcus aureus ("MRSA") (ATCC #33592)
The cultures were prepared from a lyophilized preparation according to manufacturer's instructions (American Type Culture Collection ("ATCC"), Manassas, Va.) or from stock plates. The culture was transferred into Tryptic Soy Broth (TSB, Neogen, Lansing, Mich.) and incubated at 35±2° C. for 24±2 hours. After incubation, the culture was centrifuged (Multifuge X1R, ThermoScientific, Waltham, Mass.), washed in sterile peptone water and resuspended to its original volume. The culture was plated onto Tryptic Soy Agar (TSA, Neogen) at appropriate dilutions to determine the actual final concentration.

The culture was exposed to each sanitizer, Composition A and Composition PS+, diluted with sterile DI water to a pH of 2.2 or 1.3. A separate 250 mL Erlenmeyer flask containing 99 mL of each sanitizer was prepared, along with a duplicate flask containing 99 mL of Butterfield's phosphate diluent (BPB) as a control. Sanitizer flasks were gently whirled to create residual liquid motion, and then a 1 mL aliquot of the test culture was added in the center of each flask, avoiding both the neck and sides of the flask during inoculation. Each flask was swirled for 1 minute to thoroughly mix the contents, and then a 1 mL portion of the mix was added to a 9 mL tube of a lecithin neutralizing solution, prepared as per the AOAC International (Rockville, Md.) Official Method$^{SM}$ 960.09 (Germicidal and Detergent Sanitizing Action of Disinfectants), which is incorporated by reference herein for all purposes. This procedure was repeated for the BPB control using the same challenge inoculum.

After treatment and neutralization, samples were pour plated at serial dilutions up to 10-6 (treating the neutralized tube as a 10-1) with Tryptone Glucose Extract Agar (TGEA, Neogen). TGEA plates were incubated at 36±1° C. for 27±3 hours. After incubation, plates were enumerated using a Quebec colony counter (Model #3325, Reichert Technologies, Depew, N.Y.). The numbers of observed colonies for the treated and untreated samples were recorded.

The raw count observed for each sample was converted to log 10 CFU/mL. The amount of challenge organism present in the treated samples was compared to the amount present in the control samples to determine the log reduction for each challenge organism.

The results of the testing are shown in Table 2.

TABLE 2

AOAC EVALUATION (LOGARITHMIC REDUCTION) WITH DISCLOSURE COMPOSITIONS

| | Treatment | | | |
|---|---|---|---|---|
| | Composition A | | Composition PS+ | |
| pH | 1.3 | 2.2 | 1.3 | 2.2 |
| S. aureus | 3.42 | 3.16 | >5.91 | >5.84 |
| E. coli | 3.08 | 3.60 | >5.56 | >5.67 |
| Salmonella enterica serovar Anatum | 3.1 | 3.02 | >5.7 | >5.78 |
| Listeria monocytogenes | 3.79 | 3.08 | >5.7 | >5.82 |
| MRSA | 3.93 | 3.93 | >5.73 | >5.73 |

Testing demonstrated significant antimicrobial reduction with a synergistic effect found when copper ion was combined with detergent addition. Mineral or organic acid, when buffered with a conjugate salt, yields significant antimicrobial capability without organoleptic damage when combined with copper and detergent.

Figure 3:
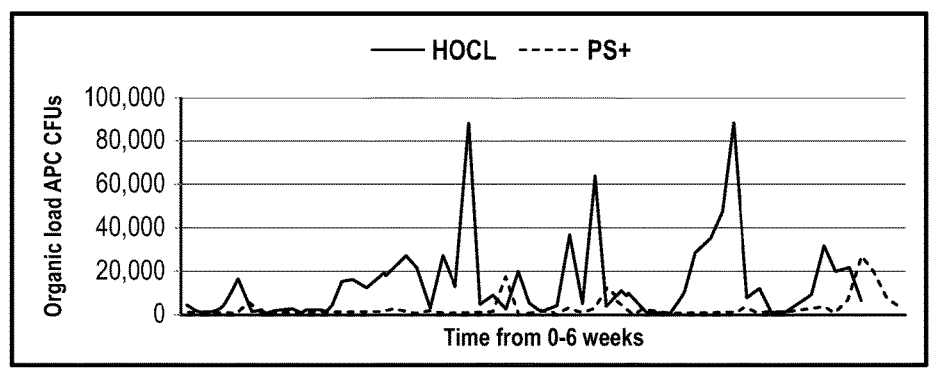
FIG. 3 depicts the results of measurements of organic load (in APC CFUs) on actual lettuce leaf surfaces from 250 randomized samples taken over a six week period. Lettuce leaf samples were treated either with a composition of the disclosure or with a standard hypochlorous acid treatment that is commonly used in the produce industry, and includes a combination of citric acid and chlorine.

Example 5: Organic Load Spike Control Through Use of Composition Invention Disclosure Versus Traditional Compositional Methods The compositions of the disclosure demonstrated significant organic load spike suppression versus traditional treatments. FIG. 3 shows the results of measurements of organic load (in APC CFUs) on actual lettuce leaf surfaces from 250 randomized samples taken over a six week period. Lettuce leaf samples were treated either with Composition PS+ of Example 2 or with standard hypochlorous acid treatment. This is of particular importance to reduce the likelihood of unexpected spikes that can lead to high levels of pathogens that may result in foodborne illness.

When ranges are used herein for physical properties, such as molecular weight, or chemical properties, such as chemical formulae, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A composition comprising:
    a mineral acid buffered with a conjugate salt;
    a copper(II) salt, wherein the copper(II) salt concentration is between about 35 ppm and about 100 ppm; and
    between 0.01 and 0.3 weight percent of an alkyl polyglycoside, based on the weight of the composition;
    wherein the composition is an aqueous solution with a pH between 1 and 4.

2. The composition of claim 1, wherein the copper(II) salt is copper (II) sulfate.

3. The composition of claim 1, wherein the mineral acid is sulfuric acid, phosphoric acid, hydrochloric acid, or a combination thereof.

4. The composition of claim 1, further comprising a buffering salt wherein the buffering salt is ammonium sulfate, sodium sulfate, sodium chloride, calcium sulfate, or a combination thereof.

5. The composition of claim 4, wherein the buffering salt concentration is between 0.05 and 0.5 weight percent, based on the weight of the composition.

6. The composition of claim 1, further comprising an antioxidant.

7. The composition of claim 6, wherein the antioxidant concentration is between 0.01 and 1 weight percent or between 0.01 and 0.05 weight percent, based on the weight of the composition.

8. The composition of claim 1, wherein the ratio of water to the remaining composition components is between about 1:1 and about 500:1 or between about 50:1 and about 500:1.

9. The composition of claim 1, wherein the composition is in the form of a solid that is a pellet, granule, powder, pod, or tablet, optionally encased in a water-soluble film or packaging, wherein the water-soluble film or packaging is a polyvinyl alcohol film, an aliphatic polyether film, or a polyethylene glycol film.

10. The composition of claim 1, wherein the pH of the aqueous solution is between 1.6 and 3.5.

11. The composition of claim 1, comprising between 0.01 and 0.25 weight percent of the alkyl polyglycoside, based on the weight of the composition.

12. A method of reducing the number of pathogens on a surface comprising applying the composition of claim 1 to the surface, wherein the surface is a foodstuff surface selected from the group consisting of a fruit, a vegetable, an algae, a seed, a grain, a sprout, a legume, soy, a nut, a meat product including a beef product and a pork product, a poultry product, a seafood product, or a dairy product.

13. The method of claim 12, wherein the pathogen is a bacterium that is optionally *Salmonella enterica, Listeria monocytogenes, Escherichia coli, Clostridium botulinum, Clostridium difficile, Campylobacter, Bacillus cereus, Vibrio parahaemolyticus, Vibrio cholerae, Vibrio vulnificus, Staphylococcus aureus, Yersinia enterocolitica, shigella*, or a combination thereof; a virus that is optionally enterovirus, norovirus, influenza, rotavirus, or a combination thereof; or a parasite that is optionally *Cryptosporidium, Toxoplasma gondii, Giardia duodenalis, Cyclospora cayetanensis, Trichinella spiralis, Taenia saginata, Taenia solium*, or a combination thereof.

14. The method of claim 12, wherein the composition is an aqueous solution at a temperature between about 32° F. and about 212° F. or between about 32° F. and about 135° F.

15. The method of claim 14, wherein the applying comprises a submersion time between about 2 seconds and about 180 seconds, between about 2 seconds and about 120 seconds, between about 2 seconds and about 90 seconds, between about 2 seconds and about 60 seconds, or between about 2 seconds and about 30 seconds.

16. The method of claim 12, wherein the applying comprises sprinkling, spraying, rinsing, soaking, immersing, or washing.

17. A method of reducing the number of pathogens in a volume of a liquid food product comprising adding the composition of claim 1 to the volume of the liquid food product.

18. The method of claim 17, wherein the pathogen is a bacterium that is optionally *Salmonella enterica, Listeria monocytogenes, Escherichia coli, Clostridium botulinum, Clostridium difficile, Campylobacter, Bacillus cereus, Vibrio parahaemolyticus, Vibrio cholerae, Vibrio vulnificus, Staphylococcus aureus, Yersinia enterocolitica, shigella*, or a combination thereof; a virus that is optionally enterovirus, norovirus, influenza, rotavirus, or a combination thereof; or a parasite that is optionally *Cryptosporidium, Toxoplasma gondii, Giardia duodenalis, Cyclospora cayetanensis, Trichinella spiralis, Taenia saginata, Taenia solium*, or a combination thereof.

* * * * *